US00PP09112P

United States Patent [19]

Frazer

[11] Patent Number: Plant 9,112

[45] Date of Patent: Apr. 18, 1995

[54] DIEFFENBACHIA PLANT NAMED PACO

[75] Inventor: Edwin J. Frazer, Queensland, Australia

[73] Assignee: Twyford International, Inc., Santa Paula, Calif.

[21] Appl. No.: 222,935

[22] Filed: Apr. 5, 1994

[51] Int. Cl.[6] ..... A01H 5/00

[52] U.S. Cl. ..... Plt./88.2

[58] Field of Search ..... Plt. 88.2

*Primary Examiner*—James R. Feyrer

*Attorney, Agent, or Firm*—Foley & Lardner

[57] ABSTRACT

A Compacta type Dieffenbachia plant named Paco characterized by its rapid growth, tolerance to high planting density, thick leaves, prominent white markings on the leaf blade and midrib, and strong stems.

1 Drawing Sheet

The present invention comprises a new and distinct cultivar of Dieffenbachia, botanically known as *Dieffenbachia hybrida,* and referred to by the cultivar name Paco.

The new cultivar is a product of a planned breeding program carried out by the inventor Edwin J. Frazer in Brisbane, Australia. The new cultivar is a product of a cross made between pollen parent Dieffenbachia Orosi Rv. 13-04, an unidentified species collected near the Orosi River, Costa Rica, and an unnamed seed parent which comprised an unnamed seedling selected from a cross of Dieffenbachia Mars×Wilson's Delight.

The cultivar was discovered from the progeny of the stated cross by Edwin J. Frazer in Brisbane, Australia. Asexual propagation by tissue culture and by division, first performed by Edwin J. Frazer in Brisbane, Australia, was used to increase the number of plants for evaluation and has demonstrated the stability of the combination of characteristics of Paco from generation to generation.

The following observations, measurements and values describe plants grown in Apopka, Fla., under greenhouse conditions which closely approximate those generally used in horticultural practice.

The following traits have been repeatedly observed to be characteristics which in combination distinguish Paco from other Dieffenbachia of the same general type, for example, the well known cultivar Compacta.

1. Paco attains a marketable size in approximately four weeks less time than Compacta.

2. Paco tolerates high planting density, and may be grown in approximately 28% less space than comparable crops of Compacta.

3. The leaves of Paco are thicker, and have more white markings on the leaf blade and midrib than Compacta.

4. The stems of Paco are stronger than those of Compacta.

All color references are measured against the Royal Horticultural Society Colour Chart. Colors are approximate as color depends on horticultural practices such as light level and fertilization rate, among others, without, however any variance in genotype.

The color photographic drawing comprises a top perspective view of a plant of Paco grown in a 15.3 cm pot, approximately 16 weeks after planting a 12 week old liner obtained by tissue culture and grown under appropriate growing conditions. Colors are as accurate as possible with color illustrations of this type.

Origin: Seedling selected from a cross of Dieffenbachia Orosi Rv. 13-04 (pollen parent), an unidentified species collected near the Orosi River, Costa Rica, and an unnamed seedling selected from a cross of Dieffenbachia Mars×Wilson's Delight (seed parent).

Classification: *Dieffenbachia hybrida,* cv Paco.

Propagation: Asexual propagation either by tissue culture or division.

Plant: In a 15.4 cm pot for a plant grown from a 12 week old liner after 16 weeks under appropriate growing conditions, Paco is approximately 15.0 cm. to 16.0 cm. from the soil surface to the junction of the petioles of the last two (2) unrolled leaves, and approximately 42 cm to 46 cm. in width.

Stem:

*Growth pattern.*—The stem is erect in growth and is 1.5 cm to 1.7 cm in diameter five (5) cm above the soil surface. Internode distance is approximately 1.1 cm to 1.7 cm three (3) cm above the soil.

*Color.*—The stem is lighter than, but closest to, 146 B–D, frequently mottled wtih 147 D.

Petiole: The following information is based on the 4th expanded leaf from the apex.

*Growth pattern.*—The petiole has fleshy edges extending from the midrib and referred to as wings. The wings are approximately 6 mm to 10 mm wide one-half the distance from the petiole base to the wing apex. The wings extend from the base of the petiole to within approximately 1.3 cm to 2.0 cm of the base of the leaf. The wings are distinctly rolled inward lengthwise where not in contact with the stem. The apex of the wings is marginate. The petiole follows the stem axis but diverges from the axis approximately 6.2 cm to 7.0 cm from the leaf base, forming a horizontal distance from the edge of the stem to the leaf base of approximately 3.1 cm to 3.9 cm.

*Dimensions.*—The petiole is often curved from the tip of the wings to the base of the leaf. The petiole is approximately 5 mm to 6 mm in diameter one-half the distance between the top of the wing and the base of the leaf. The petiole is approximately 8.9 cm to 9.4 cm in length.

*Color.*—The petiole and petiole wings are 146 A–B, often mottled with 147 D. The midrib is 147 D.

Leaf:

*Growth pattern.*—The leaf is oblong with a cuspidate apex and cordate base. The margin is entire. The leaf is asymmetric with the side of the leaf unrolling first having less surface area than the side unrolling last. The leaf is oriented parallel to the stem axis at the time of full unrolling, changing to approximately 40–45 degrees above perpendicular to the stem axis as more leaves unroll above it. The midrib is straight over two-thirds the length of the leaf and curved downward toward the tip. The leaf blade is somewhat wavy from the midrib to the margin. The leaf blades are angled upward from the midrib but flatten as the leaf ages.

*Dimensions.*—For the pot size and growing time indicated, the largest leaf is approximately 19.0 cm to 19.9 cm long and approximately 8.6 cm to 9.4 cm wide. An average sized leaf is approximately 14.0 cm to 15.3 cm long and approximately 7.7 cm to 8.0 cm wide. The leaf is moderately thick and somewhat puckered.

*Midrib.*—The leaf midrib is thick and prominent. The adaxial midrib is 155A mottled with 137 C at the junction of the petiole and the midrib. The abaxial leaf midrib is greener than, but closest to, 155 A.

*Primary veins.*—The primary veins are sunken into the adaxial surface and protrude from the abaxial surface. The primary veins are the same color as the leaf tissue surrounding them.

*Color and pattern.*—There are numerous areas of the leaf where color is significant, particularly on the adaxial surface. On the adaxial surface of new leaves, the areas of dark green are darker than but closest to 143 A, and light variegated areas are 155 A. On mature leaves, the areas of dark green are 137 A, and the light variegated areas are 145 C, 155 A. All areas become darker as the leaf ages. On the abaxial surface of new leaves, the areas of dark green are 138 B, and the light variegated areas are 145 C D. On the abaxial surfaces of mature leaves, the areas of dark green are 137 C, and the light variegated areas are 145 C. All areas darken somewhat as leaf ages.

*Axillary breaks.*—There are approximately 20 to 25 axillary breaks with at least one leaf expanded. Leaves will show color by the second leaf and will have true color and pattern by the third leaf.

*Inflorescence.*—Typical of Dieffenbachia and does not have commercial significance.

Roots: Moderately thick white roots with fine laterals.

GENERAL OBSERVATION

Dieffenbachia Paco is similar to Compacta in dimension and general appearance, but Paco reaches marketable size approximately 4 weeks sooner than Compacta, may be grown at approximately 28% greater planting density, has thicker leaves with more white markings, and has stronger stems. These combined characteristics make Paco a unique new cultivar.

I claim:

1. A new and distinct cultivar of Dieffenbachia plant named Paco, as illustrated and described.

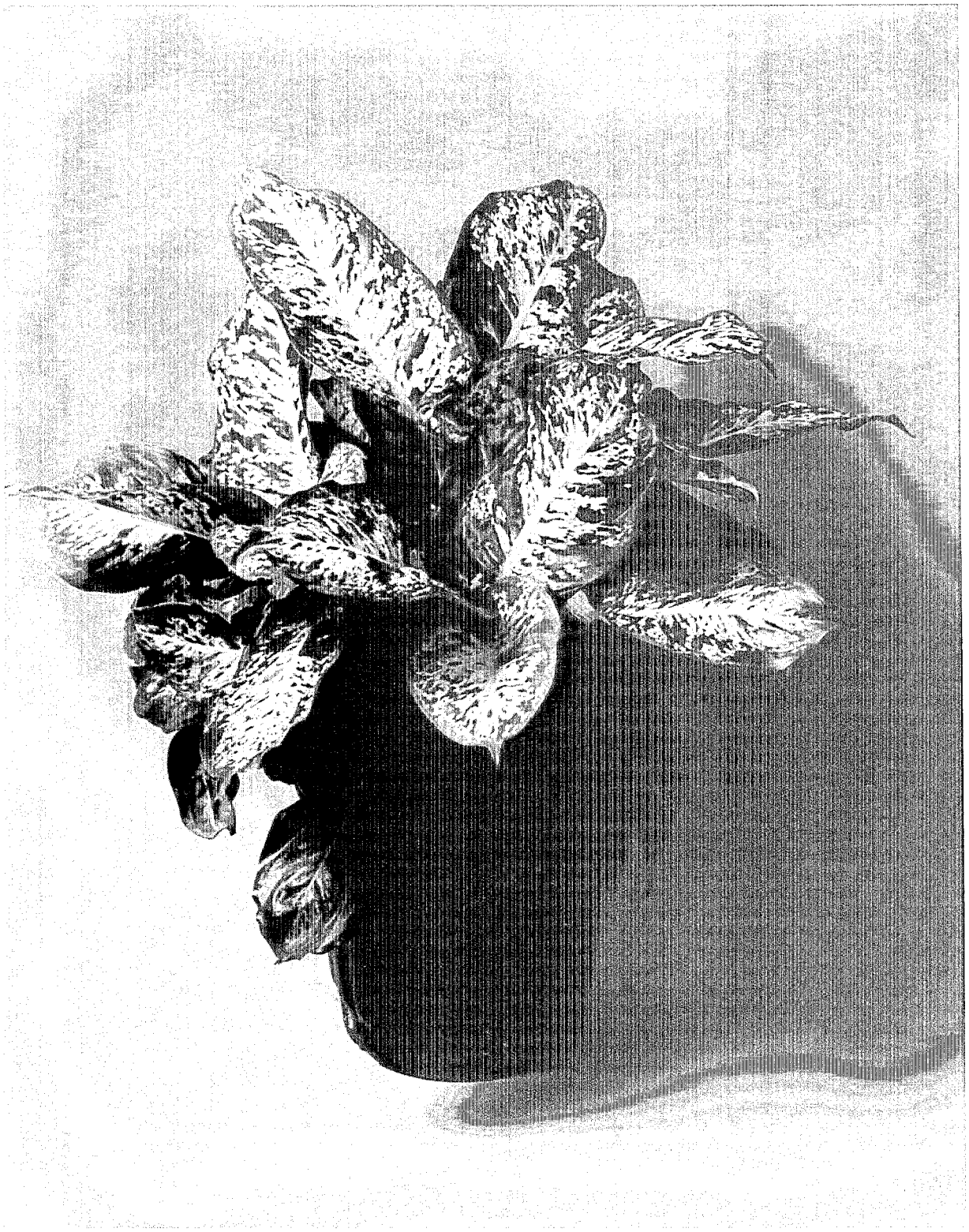

* * * * *